United States Patent [19]

Wagner et al.

[11] Patent Number: 4,489,165

[45] Date of Patent: Dec. 18, 1984

[54] CHROMOGENIC TRACERS FOR USE IN AN ASSAY

[75] Inventors: Daniel B. Wagner; Richard L. Tyson, both of Raleigh, N.C.

[73] Assignee: Becton Dickinson and Company, N.J.

[21] Appl. No.: 460,141

[22] Filed: Jan. 24, 1983

[51] Int. Cl.$^3$ .................... G01N 33/52; G01N 33/54; B65D 71/00

[52] U.S. Cl. .................................. 436/500; 436/537; 436/546; 436/800; 436/811; 436/816; 436/817

[58] Field of Search ............... 436/500, 537, 546, 800, 436/811, 816, 817

[56] References Cited

U.S. PATENT DOCUMENTS

| | | | |
|---|---|---|---|
| 4,166,105 | 8/1979 | Hirschfeld | 436/800 |
| 4,171,311 | 10/1979 | Araps | 436/800 |
| 4,279,992 | 7/1981 | Boguslaski et al. | 436/800 |
| 4,404,366 | 9/1983 | Boguslaski et al. | 436/800 |

OTHER PUBLICATIONS

Hassan et al., J. of Immunoassay, 3 (1982) 1–15.
Van Der Werf et al., J. Immunological Meth., 36 (1980) 339–347.
Al-Hakiem et al., Clin. Chem., 28 (1982) 1364–1366.

*Primary Examiner*—Christine M. Nucker
*Attorney, Agent, or Firm*—Elliot M. Olstein

[57] ABSTRACT

A chromogen, in particular, a fluorescent compound, is conjugated to a ligand through an amino acid spacer radical, which includes a free carboxyl group. The tracers are particularly suitable for use in a flow through assay for low molecular weight analytes. The tracers are rapidly bound, of good sensitivity, and low non-specific binding.

42 Claims, No Drawings

CHROMOGENIC TRACERS FOR USE IN AN ASSAY

The present invention relates to improved compositions for use in nonisotopic assays for the determination of haptens, antigens and antibodies (hereinafter referred to as "analytes") in liquid samples, including body fluids such as serum, sputum, urine and cerebral spinal fluid. The invention is particularly directed to fluorescent assays and to a method for preparing such conjugates and an improved assay method and test kit.

Immunoassay methods, in general, are based on the competition between a specific analyte, the amount of which is to be determined in the sample, and a known amount of the analyte or appropriate analog thereof in labeled form (tracer) for a limited number of available binding sites on a binder which is specific towards the analyte and tracer. Thus, in a system consisting of an unknown amount of analyte, a known amount of a tracer and a limited known amount of binder, the greater the concentration of analyte in the sample, the less the tracer will be bound by the binder.

If the concentration of tracer and binder is fixed and the only variable is the level of analyte, it is possible to establish an assay system for measuring the unknown level of analyte, by determining the amount of bound and/or free tracer in the system. Commonly used labels include radioisotopes, fluorescent dyes and enzymes. The activity of the radioisotope, the fluorescent intensity of the dye or the activity of the enzyme on a substrate is compared with the values given by a range of known amounts of the analyte treated in the same manner. The values obtained from the determination of the standard samples are used for establishing a standard calibration curve for the specific system and this curve is then used to determine an unknown concentration of the analyte in an unknown sample.

Various automatic flow through systems are also available for using labeled and unlabeled ligands. A flow through system wherein the tracer is bound to an adsorbent in a column and is elutriated in a differential pattern can be used for establishing standard calibration curves for specific systems and these curves are then used to determine an unknown concentration of analyte in a sample.

Immunoassay is a field where sensitivity is of prime importance due to the low analyte levels that are measured. Radioimmunoassay has been widely used due to the relative ease with which a ligand can be labeled with a radioisotope. Radioimmunoassay sensitivity is limited, however, to about $10^{-12}$M and is more often only in the $10^{-8}$ to $10^{-10}$M range. In addition, radiolabels suffer from the drawback of short half-life and handling hazards. There is a trend in the immunoassay field to develop nonisotopic immunoassay methods.

The sensitivity of fluorescence assays, although theoretically very high, is often limited by the presence of background fluorescence. In many situations, it is impossible to reduce the background sufficiently to obtain the desired sensitivity. The present invention is directed to providing fluorescent conjugates which are highly sensitive and which resolve many problems which have been faced by the use of fluorescence assays.

U.S. Pat. No. 4,268,663 to Skold describes macromolecular compositions which are used as glycosidase substrates. The glycosidase substrates employ a spacer arm to link a glycosidyl substituted chromophore to a macromolecular hub. The spacer arm is used to provide steric exclusion for modulating a signal in relation to the amount of analyte in an assay medium.

U.S. Pat. No. 4,329,461 to Khanna discloses fluorescent thyroid hormone conjugates of the formula

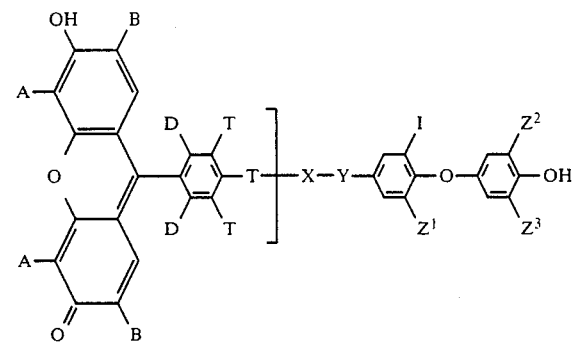

wherein:

A is any group which does not detrimentally affect the fluorescence efficiency or physical characteristics of the compound, particularly water solubility; A will normally be such groups as hydrogen, alkyl, halo, particularly of atomic number 9 to 53, more particularly of atomic number 17 to 35, and substituted alkyl, where alkyl may be substituted with halo as described previously, chalcogen of atomic number 8 to 16 (oxygen and sulfur) as hydroxy, mercapto, oxyether of from 1 to 2 carbon atoms, or thioether of from 1 to 2 carbon atoms, non-oxocarbonyl, particularly carboxy, alkoxycarbonyl, having alkoxy of from 1 to 2 carbon atoms, or carboxamide, the total number of substituents being normally of from 1 to 4, more usually from 1 to 2, wherein the alkyl groups are from 1 to 6, more usually from 1 to 2 carbon atoms.

In accordance with one aspect of the present invention, there is provided a conjugate comprised of a chromogen linked to a ligand through a defined spacer group to provide a tracer for use in an assay.

In accordance with another aspect of the invention, there is provided an assay for an analyte in which the tracer is a conjugate comprised of a chromogen linked to a ligand through a defined spacer group.

In accordance with a further aspect of the invention, there is provided an assay kit for use in an assay for an analyte which kit includes as a tracer a conjugate of a chromogen linked to a ligand through a defined spacer group.

More particularly, the tracer is comprised of a chromogen linked or conjugated to a ligand through a spacer radical derived from an amino acid having a carboxyl and/or amino substituent group in addition to the amino and carboxyl groups which are characteristic of the amino acid and in such spacer radical the carboxyl group is either in free form or exists as an appropriate salt thereof.

The spacer radical may be represented by the following structural formula:

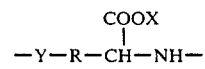

wherein X is hydrogen, an amine salt, ammonium or a metal, such as an alkali metal or alkaline earth metal

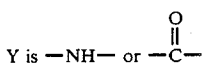

and

R is a substituted or unsubstituted divalent hydrocarbon radical having from 1 (preferably at least 2) to 13 carbon atoms, and when R is substituted the substituent group is preferably a hydrophylic group such as hydroxyl, carboxyl, amino or thio;

and wherein —R— and —CH— may be linked to form a carbocyclic chain.

The tracers produced in accordance with the present invention are represented by the following structural formula:

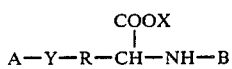

wherein:

Y, R and X are as hereinabove defined; and

A is one of the chromogen and ligand, preferably the chromogen, and B is the other of the chromogen and ligand, preferably the ligand.

Thus, the tracer is comprised of a chromogen, preferably a fluorescent compound, which functions as a marker, which is conjugated to a ligand through a spacer radical derived from an amino acid of the type hereinabove described.

In producing the conjugate, an amino group of the spacer radical is most generally conjugated to the ligand or chromogen through a suitable substituent group, such as carboxyl or carbonylchloride (amide or peptide linkage); isothiocyanate (thiourea linkage); sulfonic acid or sulfonyl chloride (sulfonamide linkage); isocyanate (urea linkage), or chloro (condensation between amino and chloro groups); and if Y is carbonyl, the carbonyl group is most generally conjugated to the ligand or chromogen through an amino substituent group (amide or peptide linkage).

As used herein, the term "analyte" refers to a hapten, antigen or antibody to be assayed.

As used herein, the term "ligand" refers to a hapten, antigen or antibody. In an assay for an analyte, the ligand, which is a portion of the conjugate used as a tracer, depending on the analyte, is either the analyte, an appropriate analog of the analyte, or a binder for the analyte.

As used herein, the term "appropriate analog" refers to an analog of the analyte which is bound by the binder used in the assay for the analyte.

The chromogen which is used as the identifiable marker for the tracer is an absorbing dye and preferably an absorbing dye which fluoresces (a fluorescent compound). It is also possible to use a non-fluorescing chromogen. The fluorescent compound includes or is provided with a substituent group which is capable of being linked to the amino or carboxyl group of the spacer radical for producing a conjugate with the ligand. The chromogens are usually aromatic compounds which may be fused or non-fused. As representative classes of fluorescent compounds there may be mentioned, for example, fluoresceins, rhodamines, coumarins, amino naphthalene derivatives (dansyl compounds), carbocyanins, indoles, lathanide chelates, etc. The following is a list of illustrative compounds (both fluorescing and non-fluorescing) which can be used as chromogens:

p-carboxy-o-nitrophenol
p-nitro-m-carboxyphenol
4-amino-6-bromo-2-naphthol
5-carboxyumbelliferone
fluorescein isothiocyanate
fluorescein amine
5(6)-carboxyfluorescein
2,6-dinitro-4-carboxyphenol
phenolphthalein isothiocyanate
5-carboxy-4',5'-dibromo-2',7'dinitrofluorescein
5-hydroxy-3-carboxymethylindole
5-hydroxy-4-chloro-7-carboxyindole
5-carboxy-3-hydroxyindole
3-carboxyindophenol
dichlorotriazinylaminofluorescein Of particular interest for use as fluorescent markers as a result of their sensitivity are fluorescein dyes, particularly fluorescein isothiocyanate, fluorescein amine, 5(6)-carboxyfluorescein and dichlorotriazinylaminofluorescein.

The selection of a suitable fluorescent marker for conjugation to a liquid in accordance with the invention is deemed to be within the scope of those skilled in the art from the teachings herein.

In producing a tracer in accordance with the present invention, R preferably has no more than 6 carbon atoms, and is most preferably alkylene. In addition, Y is preferably amino. Particularly preferred results are obtained when the spacer radical is derived from L-lysine. When deriving the spacer radical from L-lysine, the amino group adjacent to the carboxyl group is preferably conjugated to the ligand, and the remaining amino group is preferably conjugated to the fluorescent marker.

The conjugate comprised of a chromogen linked to a ligand through a spacer radical derived from an amino acid, of the type hereinabove described, may be produced by linking or conjugating the spacer radical to both the fluorescent compound and the ligand by any one of a wide variety of procedures, which are known in the art, for producing linkages of the type hereinabove described.

Thus, for example, peptide linkages may be formed by an active ester technique. Similarly, if appropriate, substituent groups may be blocked in order to provide the linkage of the desired substituent group on the amino acid. Since these procedures are well known in the art, no further details in this respect are deemed necessary for a complete understanding of the present invention. In most cases, the amino acid radical is initially conjugated to the chromogen, followed by conjugation of the chromogen-amino acid conjugate to the appropriate ligand. It is to be understood, however, that such procedure may also be reversed.

The tracers of the present invention may be employed in an assay for any one of a wide variety of analytes. The analytes, which are preferably assayed in accordance with the invention, are those having a molecular weight up to about 6,000, with the present invention being particularly suitable for analytes having a molecular weight up to about 2,000. Thus, the invention has particular applicability to assays for low molecular weight hormones and drugs, with particularly good results being obtained in an assay for $T_4$, $T_3$ and digoxin.

The binders used in the assay, in the case where the analyte is a hapten or antigen, may be an antibody or naturally occurring substance which has one or more binding sites specific for the analyte, and in the case where the analyte is an antibody, the binder may be an antigen to the antibody or an antibody elicited in response to the analyte. The selection of a suitable binder is deemed to be within the scope of those skilled in the art, and no further details in this respect are deemed necessary for a complete understanding of the invention.

In the assay, the ligand portion of the tracer used in the assay is determined by the type of assay to be employed. Thus, for example, if the assay is for an analyte which is either an antigen or hapten, the ligand portion of the tracer is either the antigen or hapten to be assayed or appropriate analog thereof. Alternatively, the ligand portion of the tracer may be a binder for the hapten or antigen to be assayed, in which case the assay is designed so that the analyte inhibits binding of the tracer to binding sites specific for the tracer.

In the case where the analyte is an antibody, the ligand portion of the tracer may be the antibody or appropriate analog thereof, in which case both the antibody and the tracer would compete for limited number of binding sites specific for both the antibody analyte and the tracer. Alternatively, the ligand portion of the tracer may be an antigen to the antibody analyte or antibody elicited in response to the antibody analyte, in which case, the antibody analyte inhibits binding of the tracer to binding sites specific for the tracer.

In some cases, where the analyte is to be determined by a so-called "sandwich type" of assay, the ligand portion of the tracer has binding sites specific for the analyte, which analyte has multiple determinant sites.

The selection of a suitable ligand for use as the ligand portion of the tracer is deemed to be within the scope of those skilled in the art from the teachings herein and, accordingly, no further details in this respect are deemed necessary for a complete understanding of the present invention.

The tracers of the present invention may be employed in any one of a wide variety of assays wherein it is possible to employ a chromogen, and in particular a fluorescent compound, as a marker. Thus, for example, a tracer may be employed in a solid phase assay, a flow through type of assay, or a homogeneous assay, with the tracer being particularly suitable for use in a flow through type of assay.

As known in the art, in one type of flow through assay, the analyte and tracer (together or sequentially) are caused to flow through a chamber, which includes a binder for the tracer supported on a solid support, whereby the tracer and analyte compete for binding sites. In another type of flow through assay, the tracer and analyte are initially contacted with a binder for the analyte and tracer, and the resulting mixture, which includes analyte and tracer bound to the binder, as well as free analyte and tracer, are caused to flow through a chamber containing a separating agent, such as an adsorbent or binder (e.g., antibody) for the tracer, supported on a solid support, whereby in the chamber the free tracer is bound or adsorbed by the separating agent and the tracer previously bound to the binder passes through the chamber.

In either case, the tracer which remains in the chamber and/or the tracer which passes through the chamber is employed as a measure of the amount of analyte in the sample being assayed.

In such flow through assays, the free tracer is in contact with the binder or separating agent in the chamber for only a short period, and applicant has found that the tracers of the present invention can be effectively used in such flow through assays; i.e., the tracer is rapidly bound to the binder and/or separating agent in the chamber.

Although the tracers are particularly suitable for use in a flow through assay, the tracers are suitable for other assays, as hereinabove described. The tracers offer the further advantage, for both flow through and other types of assays, that non-specific binding is reduced and that adverse quenching of the fluorescent portion of the tracer is avoided while maintaining binding ability of the ligand portion of the tracer. In addition, the tracer is easily prepared and has good sensitivity.

As hereinabove indicated, in accordance with the preferred embodiment of the invention, there are provided tracers for use in an assay for digoxin, $T_3$ and $T_4$, and the following are preferred tracers for use in such assays.

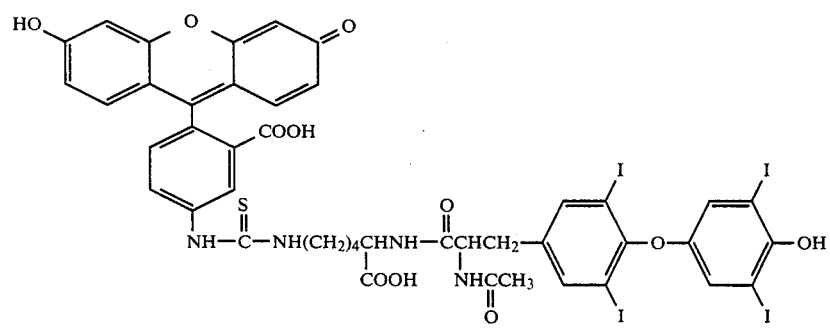

I

-continued
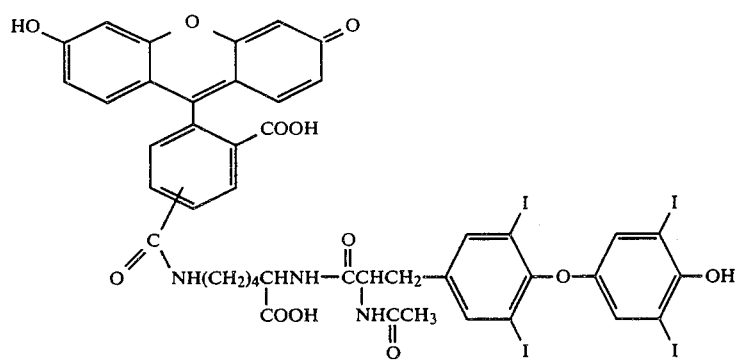
II
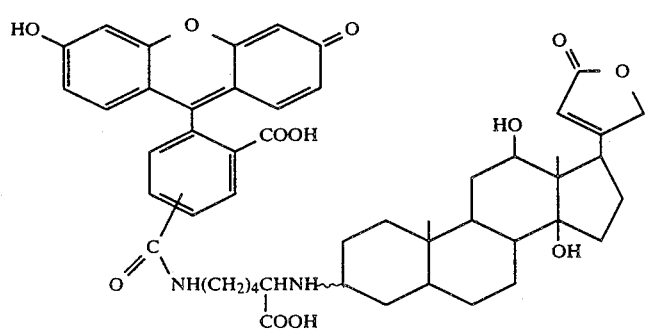
III
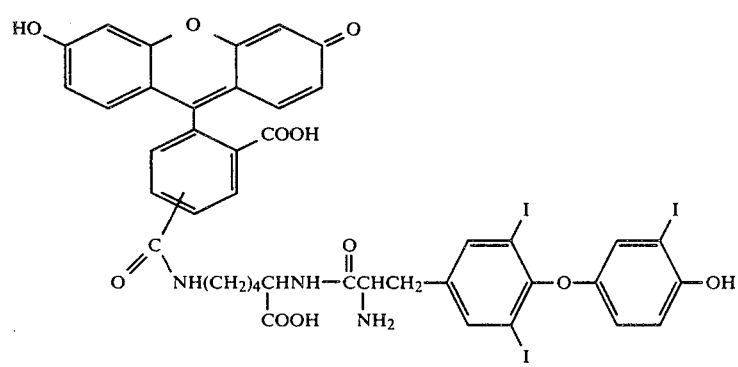
IV
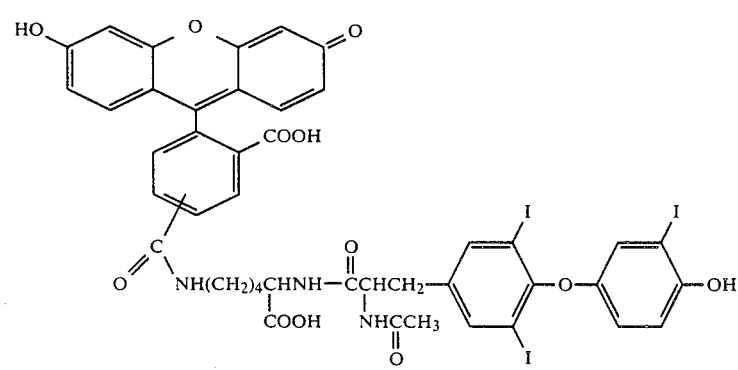
V

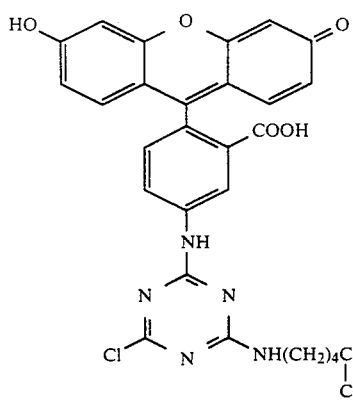

VI

In a flow through assay employed, for example, for T$_4$, and in particular a reusable flow through assay, as an illustrative example, the sample suspected of containing T$_4$ and a T$_4$ tracer of the present invention (for example, the tracer having structural formula I or II) are caused to flow through a chamber in which T$_4$ antibody is supported on a solid support, whereby a portion of the T$_4$ tracer is bound to the supported antibody in the chamber in an amount which is inversely proportional to the amount of T$_4$ in the sample. Accordingly, a portion of the T$_4$ tracer remains in the chamber bound to antibody and a portion of the T$_4$ tracer passes through the chamber. The amount of T$_4$ in the sample can be measured by determining the amount of T$_4$ tracer which has passed through the chamber and/or which is bound to antibody in the chamber, and comparing such values with those obtained by prior use of T$_4$ standard samples containing known amounts of T$_4$. The amount of tracer retained in the chamber may be determined by eluting th T$_4$ tracer from the chamber, and determining the amount of T$_4$ tracer in a suitable instrument, such as a fluorometer. In this manner, the chamber may be reused in a subsequent assay.

In a flow through assay employed, for example, for digoxin, the sample suspected of containing digoxin is incubated with a binder for digoxin (antibody) and a digoxin tracer in accordance with the present invention whereby the tracer and digoxin analyte compete for binding sites on the antibody. Subsequently, the mixture is caused to flow through a chamber in which digoxin antibody is supported on a solid support whereby previously bound tracer passes through the chamber and unbound tracer is bound by the supported antibody in the chamber. The amount of tracer which is bound in the chamber is directly proportional to the amount of digoxin analyte in the sample. Accordingly, the amount of digoxin analyte in the sample can be measured by determining the amount of tracer which passes through the chamber and/or which is bound to antibody in the chamber and comparing such values to those obtained with samples containing a known amount of digoxin analyte.

In a flow through assay employed, for example, in a T$_3$ uptake assay, a serum sample is incubated with a T$_3$ tracer in accordance with the invention, and the resulting mixture is caused to flow through a chamber in which T$_3$ binder (antibody) is supported on a solid support, with T$_3$ tracer which is bound to serum binders passing through the chamber and unbound tracer being bound to the supported antibody in the chamber. The amount of T$_3$ tracer which is bound in the chamber and/or which passes through the chamber may be employed for determining the T$_3$ uptake value of the serum by calculations generally known in the art.

Although an assay procedure has been described with reference to a T$_4$ assay, a digoxin assay and a T$_3$ uptake assay, the invention is not limited to such assays. Similarly, although a preferred embodiment has been described with respect to a flow through type of assay in which the flow through chamber includes a binder for separating bound and free components, the invention is not limited to such an assay. For example, the present invention is also applicable to a flow through type of assay in which the binder, for example, antibody, is supported on a solid support in a flow through chamber.

It is also to be understood that although an embodiment has been described with respect to a flow through type of assay, the present invention is also applicable to other types of assays, such as homogeneous assays, solid phase assays, and the like.

In accordance with another aspect of the present invention, there is provided a reagent kit or package for accomplishing an assay using a tracer of the present invention. The kit would include as specific components, a tracer of the type hereinabove described, as well as a binder, in particular an antibody, for the analyte to be assayed, with such binder being present either supported on a solid support, or in unsupported form. The kit components, where applicable, are included in the reagent kit or package in separate containers; for example, vials. The kit may also include other components such as standards of the analyte (analyte samples having known concentrations of the analyte; buffers; and the like).

In a kit designed for use in a flow through assay, the kit would include a flow through chamber which includes a binder for the analyte supported on a solid support. Thus, for example, a kit for a T$_4$ assay may include a T$_4$ tracer of the type hereinabove described and a T$_4$ binder; in particular an antibody, supported on a solid support in a flow through chamber.

The invention will be further described with respect to the following examples; however, the scope of the invention is not to be limited thereby.

Unless otherwise indicated, all of the temperatures are in centigrade, all percents and parts are by weight, except for mixtures of liquids, which are by volume. The following abbreviations are employed:

m mol = milliliter
ml = milliter
g = gram tlc = thin layer chromatography
$R_f$ = rate of flow
M = molarity
u = micron
cm = centimeter
mm = millimeter
mg = milligram
N = normality
Å = angstrom
t-BOC = tertiary butyloxycarbonyl
FITC = fluorescein isothiocyanate
DTAF = dichlorotrizinylaminofluorescein
MeOH = methanol
Si gel = silica gel
EtOAc = ethyl acetate
$CHCl_3$ = chloroform
$CH_2Cl_2$ = dichloromethane
THF = tetrahydrofuran
HOAc = acetic acid
$MgSO_4$ = magnesium sulfate
$Na_2SO_4$ = sodium sulfate
$NaHCO_3$ = sodium bicarbonate
$H_2O$ = water

EXAMPLE 1

FLUORESCEIN ISOTHIOCYANATE-LYSINE-N-ACETYL-L-THYROXINE CONJUGATE

A. α-t-BOC-L-lysine (2.46 g, 10.0 m mol) was dissolved in 50 ml of 10% triethylamine in water, and the resulting solution was cooled to 0°. To the cold solution was added in one portion 1.00 g (2.56 m mol) of FITC. The reaction mixture was allowed to warm to room temperature and remain there for an additional 30 min. The reaction mixture was treated with 200 ml of ethyl acetate followed by solid citric acid until the pH of the aqueous phase reached 2.0. The organic layer was separated and washed with water (3 × 100 ml) and brine (100 ml). Evaporation of the solvent afforded FITC-ε-(α-t-BOC-L-lysine) as a yellow solid that was quite pure by tlc (Si gel, 20% MeOH/$CHCl_3$).

The FITC-lysine was dissolved in 20 ml of trifluoroacetic acid followed by 20 ml of $CH_2Cl_2$, and the reaction mixture was allowed to stir at room temperature for 3 hrs. Tlc analysis (Si gel, 20% MeOH/$CHCl_3$) indicated the absence of starting material, and the solution was evaporated to dryness. The residue was dissolved in 10 ml of MeOH, and the methanolic solution was added dropwise to 1 liter of vigorously stirred ether. The bright yellow precipitate was collected by suction filtration and washed with a small quantity of dry ether. The MeOH/ether precipitation precedure was repeated twice. The product FITC-ε-L-lysine was nearly pure by tlc analysis (Si gel, 85:10:5 acetone-water-acetic acid).

A solution of 0.433 g (0.529 m mol) of N-acetyl-L-thyroxine in 10 ml of anhydrous THF under a nitrogen atmosphere was treated successively with 0.0669 g (0.581 m mol) of N-hydroxysuccinimide and 0.131 g (0.634 m mol) of dicyclohexylcarbodiimide. The reaction mixture was allowed to stir at room temperature for 2.0 hr and then rapidly filtered (fine sintered glass). The filtrate was evaporated, and the crude active ester was immediately dissolved in 10 ml of anhydrous pyridine. To the pyridine solution was added 0.283 g (0.529 m mol) of FITC-ε-L-lysine, and the reaction mixture was allowed to stir at room temperature under nitrogen for 40 hr. Solvent was removed by evaporation, and the residue that remained was dissolved in ethanol and the solution evaporated to remove residual pyridine. This procedure was repeated to yield 0.794 g of the crude conjugate as a yellow-orange foam. A portion of the crude product (90 mg) was chromatographed on two 20×20 cm silica gel preparative-layer plates (2.0 mm, EM) developing twice with 85:10:5 $CHCl_3$—MeOH—HOAc. Two major yellow bands were observed and isolated by extraction with MeOH. Tlc analysis (Si gel, 85:10:5 $CHCl_3$—MeOH—HOAc) indicated that both the high $R_f$ (0.50) component and the low $R_f$ component (appeared as two close running spots at $R_f$ = 0.27 and 0.21) were quite pure. The compound of higher $R_f$ showed significant binding in the bioassay test system.

EXAMPLE 2

CARBOXYFLUORESCEIN-LYSINE-N-ACETYL-L-THYROXINE CONJUGATE

N-Acetyl-L-thyroxine (0.500 g) was dissolved in 12 ml of anhydrous THF under an inert atmosphere, and 0.077 g of N-hydroxysuccinimide followed by 0.151 g of dicyclohexylcarbodiimide were added. The reaction mixture was allowed to stir at room temperature and then rapidly filtered through a fine sintered glass funnel. Evaporation of the filtrate afforded a colorless glass that contained no free acid by tlc (Si gel, EtOAc). The active ester was used immediately without further purification.

The active ester of L-thyroxine was dissolved in 10 ml of anhydrous pyridine, and 0.308 g of 5(6)-carboxyfluorescein-ε-lysylamide was added. The reaction mixture was allowed to stir under an argon atmosphere overnight. The yellow solution was evaporated, and the residue that remained was suspended in dilute citric acid (pH 3). The aqueous phase was extracted with EtOAc containing a small quantity of MeOH (2×50 ml). The organic extracts were combined, dried ($MgSO_4$) and evaporated to yield the crude conjugate as a yellow foam (0.868 g) that appeared as one major yellow spot and several minor spots upon tlc analysis (Si gel, 80:15:5 $CHCl_3$—MeOH—HOAc).

The crude conjugate (0.050 g) was chromatographed on a silica gel, preparative, thin-layer plate (EM, 2.0 mm) with two developments in 85:14:1 $CH_2Cl_2$—MeOH—HOAc. The major yellow band was isolated and the product extracted with MeOH. The solvent was evaporated, the residue dissolved in a minimum quantity of MeOH, and the solution filtered through a 0.45u filter pad. Evaporation of the filtrate afforded 0.043 g of the yellow-orange conjugate. A small quantity of the conjugate was further purified by chromatography on 20×20 cm analytical, thinlayer plates using the solvent described above. The carboxyfluorescein-lysine-N-acetyl-L-thyroxine conjugate was pure by tlc (Si gel, 85:14:1 $CH_2Cl_2$—MeOH—HOAc).

EXAMPLE 3

CARBOXYFLUORESCEIN-LYSINE-DIGOXIGENIN CONJUGATE

5(6)-Carboxyfluorescein (7.5 g, Eastman) was dissolved in 100 ml of dry pyridine and 3.45 g of N-hydroxysuccinimide, and 6.2 g of dicyclohexylcarbodiimide were added successively. The reaction mixture was allowed to stir at room temperature for 2 hr and then diluted with 100 ml of EtOAc, filtered, and evaporated almost to dryness. The residue was partitioned between EtOAc and acidified (citric acid) NaCl solution. The EtOAc layer was washed with saturated brine, dried, and evaporated. The residue was dissolved in 3:1 EtOAc—CHCl$_3$, and a small quantity of insoluble material was removed by filtration. The solution was applied to a silica gel column prepared in the same solvent. After a small forecut containing fast-moving impurities, the N-hydroxysuccinimide ester was eluted (8.1 g).

α-t-Boc-lysine (2.95 g) was dissolved in 30 ml of carbonate/bicarbonate buffer (0.5N, pH 9.5). A solution of 2.36 g of the active ester of carboxyfluorescein in 40 ml of pyridine was added dropwise during 5 min to the lysine/buffer solution. The reaction mixture was allowed to stir at room temperature for 15 min and evaporated. The residue was partitioned between EtOAc and 10% aqueous citric acid. The organic layer was washed with water until neutral and then washed with saturated brine, dried and evaporated. The residue was dissolved in 50 ml of 1:1 trifluoroacetic acid/CH$_2$Cl$_2$. The reaction mixture was allowed to stir for 1 hr at room temperature. The dark solution was evaporated, and the residue that remained was dissolved in 20 ml of MeOH. The methanolic solution was added dropwise during 5 min to 1000 ml of rapidly stirred ether. The brilliant yellow precipitate was collected by suction filtration, washed with ether, and dried to afford 1.71 g of the 5(6)-carboxyfluorescein-e-lyslyamide. The product was reasonably pure by tlc (Si gel, 3:1 MeOH—Acetone).

A solution of 5(6)-carboxyfluorescein (504 mg, 0.82 m mole) in 30 ml of methanol containing 194 mg (2.36 m mole) of sodium acetate was added with stirring to a solution of 3-ketodiogoxigenin (350 mg, 2.19 m mole) in 30 ml methanol. A few minutes following the addition, a solution of sodium cyanoborohydride (50.7 mg, 0.81 m mole) in 1.0 ml methanol was added, and after brief stirring, the reaction mixture was allowed to stand over 4Å molecular sieves overnight. The reaction mixture was filtered and evaporated to dryness. The residue that remained was suspended in 100 ml of water. Solution was effected by the addition of 0.05M NH$_4$HCO$_3$ (pH 8.5) buffer. The aqueous solution was extracted with ethyl acetate (2×150 ml) in order to remove the excess 3-ketodigoxigenin. The aqueous phase was then lyophilized to afford the crude conjugate (1.1 g). The crude product was dissolved in methanol and absorbed onto a small amount of silanized silica gel 60. The dry powder was applied to the top of a column packed with silanized silica gel 60 equilibrated in 5% H$_2$O/acetonitrile. An elution gradient of 5 to 15% H$_2$O in acetonitrile was employed. The chromatographic purification yielded 5(6)-carboxyfluorescein-lysinedigoxigenin conjugate as a yellow-orange powder (545 mg). All analytical data obtained (NMR, IR, UV, TLC, HPLC) are consistent with the proposed structure. Anal. Calcd. for C$_{50}$H$_{56}$N$_2$O$_{12}$.5H$_2$O. C, 62.13%; H, 6.88%, N, 2.90%. Found: C, 62.88%; H, 6.80%, N, 3.34%.

EXAMPLE 4

CARBOXYFLUORESCEIN-LYSINE-3,3',5-TRIIODO-L-THYRONINE CONJUGATE

Five ml of thionyl chloride were added to a solution of 1.0 g 5(6)-carboxyfluorescein-ε-lysylamide in 50 ml of anhydrous MeOH, and the solution was cooled in a dry-ice acetone bath. After stirring for 5 min, the cooling bath was removed, and the reaction mixture was kept at 40°-50° C. for 2 hr. The solid which was left upon evaporation was chromatographed on a silica gel column eluting with chloroform:MeOH 4:1 to yield 0.51 g of the methyl ester.

A solution of 3,3',5-triiodo-N-trifluoroacetyl thyronine (2.2 g) in 30 ml of anhydrous pyridine was treated with 0.60 g of dicyclohexylcarbodiimide, followed by 0.50 g of the methyl ester of 5(6)-carboxyfluorescein-ε-lysylamide. The reaction mixture was kept at room temperature for 2 hr, and the solid which was left upon evaporation of the volatiles was partitioned between ethyl acetate and brine, acidified with 10% citric acid. The organic layer was washed with water (to pH 4.0) and with brine. The solid dicyclohexylurea was removed by filtration, and the ethyl acetate solution was evaporated to dryness, affording the crude, protected conjugate.

The crude conjugate was dissolved in a 1M solution of morpholine in MeOH (50 ml), and the reaction mixture was left at room temperature overnight. Ten ml of 2N NaOH solution were added, and the dark orange solution was left at room temperature for 6 hr. The solid which was left on evaporation of the volatiles was partitioned between ethyl acetate and 10% citric acid solution. The organic layer was washed with brine, dried, and evaporated to dryness. The residue was partially purified by column chromatography (silica gel, gradient chloroform:MeOH 1:1 to pure MeOH) to give the carboxyfluoresceinlysine-3,3',5-triiodo-L-thyronine conjugate.

EXAMPLE 5

CARBOXYFLUORESCEIN-LYSINE-3,3',5-TRIIODO-N-ACETYL-L-THYRONINE CONJUGATE

To a solution of 0.508 g of 3,3',5-triiodo-N-acetyl thyronine in 20 ml of anhydrous THF were added 0.091 g of N-hydroxysuccinimide and 0.179 g of dicyclohexylcarbodiimide. The resulting reaction mixture was allowed to stir at room temperature under an argon atmosphere for 18 hr. The reaction mixture was rapidly filtered and evaporated to yield the crude ester which was used without further purification.

The N-hydroxysuccinimide ester was dissolved in 7 ml of anhydrous pyridine, and 0.364 g of 5(6)-carboxyfluorescein-ε-lysylamide was added to the stirring solution. The reaction mixture was allowed to stir at room temperature under an argon atmosphere for 18 hr. The reaction mixture was evaporated and the residue treated with EtOH. Solvent evaporation afforded the crude conjugate as a gummy, yellow solid. The crude product was partitioned between EtOAc (30 ml), and aqueous citric acid (30 ml). The aqueous phase was extracted with two additional 50 ml portions of EtOAc, and all organic extracts were combined, dried, and evaporated to yield 1.03 g of a yellow solid that appeared as several spots on tlc (Si gel, 75:21:4 CH$_2$Cl$_2$—MeOH—AcOH).

A small portion (0.050 g) of the conjugate was chromatographed on a silica gel, preparative plate (EM, 2.0 mm) developing with 75:21:4 CH$_2$Cl$_2$MeOH—AcOH. The two major yellow bands were isolated affording 0.014 g of the higher R$_f$ component and 0.022 g of the lower R$_f$ component, both pure by tlc (Si gel, solvent as above).

EXAMPLE 6

DICHLOROTRIAZINYLAMINOFLUORESCEIN (DTAF)-LYSINE-DIOGOXIGENIN CONJUGATE

α-t-BOC-lysine (1.39 g, 5.64 mmol) was dissolved in 50 ml of 9:1 water-triethylamine, and the solution was cooled to 0° with an ice-water bath. A single portion (1.00 g, 1.88 mmol) of DTAF was added, and the reaction mixture was allowed to stir at 0° for 1.0 hr. The solution was poured into 200 ml of EtOAc, and aqueous citric acid solution was added until the pH of the aqueous phase was approximately 4. The layers were separated, and the aqueous layer was extracted with 100 ml of EtOAc. The combined organic layers were washed with 100 ml of water, dried ($MgSO_4$) and evaporated affording 1.22 g of the DTAF-lysine derivative as an orange foam. The crude product was dissolved in a small volume of MeOH and precipitated by the addition of ether-hexane.

The t-BOC protecting group was removed by treating the product with 10 ml of 1:1 trifluoroacetic acid/$CH_2Cl_2$ for 1.0 hr. The reaction mixture was evaporated and the residue dissolved in EtOH. Evaporation of the EtOH followed by vacuum-drying of the residue yielded 1.0 g of the DTAF-ε-lysine derivative as a yellow-orange solid. The product was reasonably pure by tlc (Si gel, 70:20:5 $CHCl_3$—MeOH—HOAc).

A solution of 100 mg (0.132 mmol) of DTAF-ε-lysine in 5 ml of anhydrous MeOH was treated with several 4Å A molecular sieves and 56 μl (0.40 mmol) of triethylamine. Following the addition of base, a suspension of 51.4 mg (0.132 mmol) of 3-ketodigoxigenin in 2 ml of MeOH was added, and the reaction mixture was allowed to stir under nitrogen for 30 min. A solution of 1.0 ml of MeOH containing 8.76 mg (0.132 mmol) of sodium cyanoborohydride was added, and the mixture was allowed to stir at room temperature for 17 hr. A small quantity of insoluble material was removed by suction filtration, and the filtrate was evaporated affording 137 mg of a gummy, red solid. A small quantity of the crude conjugate was chromatographed on two 20×20 cm, silica gel, analytical plates (EM) developing with 80:40:1 acetone-MeOH-HOAc. The major, yellow band was extracted with 2:1 acetone-MeOH to afford, following evaporation, the DTAF-lysine-digoxigenin conjugate as a yellow solid. The conjugate was homogeneous by silica gel tlc analysis (2:1 acetone-MeOH with trace HOAc).

The following examples are illustrative of assays employing tracers of the present invention. The assays are particularly described with reference to the Automated Instrument sold by Becton Dickinson Immunodiagnostics under the ARIA mark; however, the scope of the invention is not limited thereby. The instrument uses a flow through chamber.

EXAMPLE 7

DIGOXIN ASSAY

I Reagents.
1. Adsorption Buffer #5, pH 7.4.
   ARIA reagent—Catalog No. 614335. Contains phosphate, sodium chloride, and preservative.
2. Elution Buffer #4, pH 10.2.
   ARIA reagent—Catalog No. 614211P. Contains 50% methyl alcohol, glycine buffer, and preservative.
3. Digoxin Standards.
   ARIA reagent—Catalog No. 612839. Contains digoxin in stabilized human plasma with preservatives.
4. Digoxin Antibody Chamber.
   ARIA reagent—Catalog No. 630519. Contains digoxin antibody covalently bonded to cellulose.
5. Digoxin Fluorescent Tracer. (Tracer of Example 3)
   Diluted in Adsorption Buffer #5, pH 7.4 (Reagent #1).
6. Digoxin Polyclonal Antibody.
   Diluted in Adsorption Buffer #5, pH 7.4 (Reagent #1).
7. Distilled water.

II. Instrument Setup.
1. Insert DISC 2 into disc reader. Read File 27 into the computer.
2. Place reagent bottles containing sufficient volumes for the entire run on the instrument as follows:
   Blue Cap—Adsorption buffer #5, pH 7.4 (Reagent #1).
   Yellow Cap—Distilled water (Reagent #7).
   Red Cap—Elution buffer #4, pH 10.2 (Reagent #2).
   Green Ring—Digoxin fluorescent tracer (Reagent #5).
   Brown Ring—Digoxin polyclonal antibody (reagent #6).
3. Ensure that the Beta/Gamma valve is pulled out into the GAMMA position.
4. Ensure that the G-H valve is pulled out to the H position.
5. If this is the first digoxin run, insert two priming blanks into the antibody and prefilter positions, and perform priming routine (OP CODE 9).
6. After priming has been completed, remove priming blanks, and attach two antibody chambers to the antibody and the prefilter positions.
7. Pipet 125 ul of standards controls and patient samples into sample cups and cap with cone-shaped caps.
8. Load carousel with sample cups as follows:

Inner Ring:

| Position No. | Contents |
| --- | --- |
| *101 | 350 ul zero standard |
| 102, 103 | adsorption buffer #5 |
| 104–106 | zero standard |
| 107, 108 | 0.5 mg/ml std |
| 109, 110 | 1.0 mg/ml std |
| 111, 112 | 2.0 mg/ml std |
| 113, 114 | 4.0 mg/ml std |
| 115, 116 | 8.0 mg/ml std |
| 118– | patient samples |
| **Last ten cups of run | adsorption buffer #5 |

*Once tracer, sample, antibody, and buffer have been pipetted into the reaction cup, the run is aborted, the reaction cup removed, saved, and replaced with an empty reaction cup. This is repeated again. The third time the machine is started, the run continues uninterrupted. Once buffer from position 102 and 103 are transferred to the reaction cups, the reaction cups are replaced with the reaction cups prepared by the machine initially giving three maximum binding samples.

**The last ten buffer cups are used in the assay to eliminate the gather phase of the program. The first two are replaced with reaction cups containing 100 ul standard and 555 ul adsorption #5 which will be used for serum blanks.

Outer Ring:

Place sufficient number of empty reaction cups for entire assay.

III. Programming.
  1. Go through OP CODE 20 for new reagents.
  2. Select OP CODE 13; begin with number 101 and end with the final assay sample number.
  3. The final sample number may be changed during the assay by utilizing BREAK-BREAK-2-3.
  4. The assay can be aborted by utilizing BREAK-BREAk-2-3.
IV. Sample Collection.
  A fraction collector is hooked up to the ARIA so that all reagents passing through the antibody chamber are collected as follows:

| Tube # | Contents |
|---|---|
| 1. | 5.4 ml of buffer |
| *2. | 950 ul of eluted sample |
| 3. | 950 ul of elution buffer |

*Tube 2 is taken, vortexed, and read on the fluorometer.

V. Fluorescence Determination—PE 650
  A. Instrument Settings
    Excitation=488 nm slit=10
    Emission=515 nm slit=15
  B. Calibrate 950 ul volume using the time (seconds) dial on the controller. Fill about 5 tubes with 950 ul glycine methanol buffer, sample, and aspirate long enough to get entire sample through the cuvette without drawing air bubbles (vacuum gauge should be at 17 psi).
  C. With time delay at 60 seconds, aspirate the first maximum binding tube, and set instrument so meter reads approximately 1200.
  D. Set time delay at 30 seconds and read remainder of tubes.
VI. Calculations. A. Subtract each value from the average maximum binding value. This will give the net fluorescence equivalent to the first bound (or soluble bound) fraction. B. Divide each value from A. by the average net fluorescence of the zero standards to give you the $B/B_o$ values. C. Plot the $B/B_o$ values for the standards on log/logit paper, and calculate the concentration of digoxin in the unknowns.
VII. Notes.
  1. Total tubes are prepared by taking 94.7 ul of the tracer dilution diluted to 950 ul with glycine methanol buffer. These are used to determine maximum column binding:

$$\frac{Fl_{Max.Bind} - Fl_{S.B.}}{Fl_{Total} - Fl_{G/M}} = \text{Column Binding}$$

2. To determine percent binding of soluble antibody:

$$\frac{Net_{Fluor} \text{ of Zero (1st Bound)}}{Fl_{Max.Bind.} - Fl_{S.B.}}$$

EXAMPLE 8

T4 ASSAY

I. Reagents.
  1. Elution Buffer #4, pH 10.2.
    ARIA reagent—Catalog No. 614211P. Contains 50% methyl alcohol, glycine buffer, and preservative
  2. Adsorption Buffer #2, pH 10.4–10.6.
    ARIA reagent—Catalog No. 601217. Contains glycine buffer, BSA and preservative.
  3. Rinse Solution #1.
    ARIA reagent—Catalog No. 602019. Contains 40% methanol solution.
  4. Sample Buffer #4 with 450 mg/l ANS.
    ARIA reagent—Catalog No. 60198P. Contains glycine buffer, ethyl alcohol, 0.03% ANS, and preservative. Additional 450 mg/l ANS added.
  5. T-4 Fluorescent Tracer. (Example 2)
    Diluted in Sample Buffer #4 with ANS (Reagent #4).
  6. Thyroxine Antibody Chamber.
    ARIA reagent—Catalog No. 600512. Contains thyroxine antibody covalently bonded to glass beads.
  7. Thyroxine Standards.
    ARIA reagent—Catalog No. 624179. Contains thyroxine in stabilized human serum with preservatives.
  8. Thyroxine Stock Solution.
    Dissolve 5 mg of thyroxine in approximately 0.5 ml of 0.5N NaOH. Once dissolved, dilute in 100 ml distilled water.
II. Instrument Setup.
  1. Insert Disc 2 into disc reader. Read File 18 into the computer.
  2. Place reagent bottles containing sufficient volumes for the entire run on the instrument as follows:
    Blue Cap—Elution Buffer #4, pH 10.2 (Reagent #1).
    Red Cap—Adsorption Buffer #2, pH 10.4–10.6 (Reagent #2).
    Yellow Cap—Rinse Solution #1 (Reagent #3).
    White Cap—Sample Buffer #4 with ANS (Reagent #4).
    Brown Cap—T-4 Fluorescent Tracer (Reagent #5).
  3. Ensure that the Beta/Gamma valve is pulled out into the GAMMA position.
  4. Ensure that the G-H valve is pushed in to the G position.
  5. If this is the first T-4 run, insert two priming blanks into the antibody and prefilter positions, and perform priming routine (OP CODE 9).
  6. After priming has been completed, remove priming blanks, and attach two antibody chambers to the antibody and the prefilter positions.
  7. Pipet 200 ul of standards controls and patient samples into sample cups and cap with cone-shaped caps.
  8. Load carousel with sample cups as follows:

Outer Ring

| Position No. | Contents |
|---|---|
| 1–4 | 0 ug/dl std |
| 5–6 | 1.0 ug/dl std |
| 7–8 | 2.0 ug/dl std |
| 9–10 | 3.0 ug/dl std (1:1 dilution of 2.0 & 4.0 ug/dl std) |
| 11–12 | 4.0 ug/dl std |
| 13–14 | 8.0 ug/dl std |
| 15–16 | 16.0 ug/dl std |
| 17–18 | 24.0 ug/dl std (1:1 dilution of 16.0 & 32.0 ug/dl std) |
| 19–20 | 32.0 ug/dl std |
| 21– | serum samples |
| Last 2 cups of run | 200 ul of 0 std + 20 ul stock T-4 solution |

III. Programming.
  1. Go through OP. CODE 20 for new reagents.
  2. Select OP CODE 13; begin with number 1 and end with the final assay sample number.
  3. The final sample number may be changed during the assay by utilizing BREAK-BREAK-2-3.
  4. The assay can be aborted by utilizing BREAK-BREAK-2-3.

IV. Sample Collection.
A fraction collector is hooked up to the ARIA so that all reagents passing through the antibody chambers are collected as follows:

| Tube # | Contents |
| --- | --- |
| 1. | 5.24 ml of buffer |
| *2. | 1.46 ml of eluted sample |
| 3. | 1.65 ml of buffer |

*Tube #2 is taken, vortexed, and read on the fluorometer.

V. Fluoroescence Determination—PE 650.
  A. Excitation=488 nm/slit=10
     Emission=515 nm/slit=15
  B. Calibrate to 1.46 ml using the time dial on controller. Fill about 5 tubes with 1.46 ml of G/M buffer and aspirate long enough to get entire sample through the cuvette without drawing air bubbles (vacuum gauge should be at 17 psi).
  C. Aspirate first tube (zero std) and adjust sensitivity to read about 1300. (Time delay set at 60 sec.)
  D. Readjust time delay to 30 sec. and read remainder of tubes.
  E. Total tubes are prepared by taking 180 ul of tracer plus 1.280 ml of Elution Buffer 4.

VI. Calculations.
  A. Subtract the NSB (average) from all standard and serum values.
  B. Divide each value obtained in A. by the average of 3 zeros to give the $B/B_o$ value.

$$\frac{\text{Net Fluorescence of Unknown}}{\text{Ave. Net Fluorescence of 0 ug/dl Std.}} = B/B_o$$

C. Plot the $B/B_o$ values for the standards on log/logit paper, and calculate the concentration of T-4 in the unknowns.

$$\frac{\text{Net Fluorescence of 0 ug/dl Std.}}{\text{Total Fluorescence} - \text{G/M Blk.}} = \% \text{ Column Binding}$$

EXAMPLE 9

T3 UPTAKE PROCEDURE

I. Reagents.
  1. Barbital Buffer, pH 8.6, 0.075M.
     15.45 gm. Na-Barbital diluted to 1 liter with distilled water. pH to 8.6 using phosphoric acid, 85% (Fisher Scientific #A-242).
  2. Elution Buffer #4, pH 10.2.
     ARIA reagent—Catalog No. 614211P. Contains 50% methyl alcohol, glycine buffer and preservative.
  3. T-3 Fluorescent Tracer. (Example 4)
     Diluted in barbital buffer, pH 8.6, 0.075M (Reagent #1).
  4. T-3 Antibody Chamber.
     ARIA reagent—Catalog No. 609315. Contains triiodothyronine antibody covalently bonded to a solid support
  5. T-3 Uptake Prefilter.
     ARIA reagent—Catalog No. 609218. Contains filtering material
  6. Thyrotrol Controls. (Pooled normal serum) Nuclear Medical Laboratories II. Instrument Setup.
  1. Insert DISC 3 into disc reader. Read File 12 into the computer.
  2. Place reagent bottles containing sufficient volumes for the entire run on the instrument as follows:
     Blue Cap—Barbital buffer, pH 8.6, 0.075M (Reagent #1).
     Yellow Cap—Barbital buffer, pH 8.6, 0.075M (Reagent #1).
     Red Cap—Elution buffer #4, pH 10.2 (Reagent #2).
     Green Ring—T-3 Fluorescent tracer (Reagent #3).
     Brown Ring—Barbital buffer, pH 8.6, 0.075M (Reagent #1).
  3. Ensure that the Beta/Gamma valve is pulled out into the GAMMA position.
  4. Ensure that the G-H valve is pulled out to the H position.
  5. If this is the first T-3 Uptake run, insert two priming blanks into the antibody and prefilter positions and perform priming routine. (OP CODE 9).
  6. After priming has been completed, remove priming blanks, and attach the antibody chamber and the prefilter to the appropriate position.
  7. Pipet 75 ul of controls and patient samples into sample cups and cap with cone-shaped caps.
  8. Load carousel with sample cups as follows:

Inner Ring

| Position No. | Contents |
| --- | --- |
| *101–103 | Barbital buffer |
| 104, 105 | Hypo control |
| 106, 107 | Normal control |
| 108, 109 | Hyper control |
| 110– | Patient samples |
| **Last 3 cups of run | Barbital buffer |

*Once tracer, sample, buffer have been pipetted into the reaction cups, they are replaced with blanks containing 50 ul of serum and 605 ul of barbital buffer.
**Last three cups used to determine maximum binding.

Outer Ring

Place sufficient number of empty reaction cups for entire assay.

III. Programming.
  1. Check to be sure that two incubation cups are indicated, using OP CODE 33.
  2. Select OP CODE 13, begin with number 101 and end with the final assay sample number.
  3. The final sample number may be changed during the assay by utilizing BREAK-BREAK-2-3.
  4. The assay can be aborted by utilizing BREAK-BREAK-2-3.

IV. Sample Collection.
A fraction collector is hooked up to the ARIA so that all reagents passing through the prefilter and antibody chamber are collected as follows:

| Tube # | Contents |
| --- | --- |
| 1. | 5.4 ml of buffer wash |
| *2. | 800 ul eluted sample |
| 3. | 1.1 ml elution buffer |

*Tube #2 is taken, vortexed, and read on the fluorometer.

V. Fluorescence Determination—PE 650.
  A. Excitation=488 nm/slit=10
     Emission=515 nm/slit=15
  B. Calibrate 800 ul volume using the sampling time dial on controller. Fill about 5 tubes with 800 ul of EB #4 buffer, sample, and aspirate long enough to get sample through the cuvette without drawing air bubbles (vacuum gauge should be at 17 psi).
  C. Elution tubes #1 through #4 should be read at sensitivity settings of Range: 3 Fine: 5. The remaining elution tubes should be read at sensitivity Range: 1 Fine: 5 with time delay of 30 seconds.
  D. Total tubes are prepared by taking 94.7 ul of tracer dilution, diluted to 800 ul with EB #4, and are read at the end of the elution tubes at sensitivity of 0.3/5.

VI. Calculations.
  A. Average the serum blank fluorescence and subtract from each control and unknown to obtain net fluorescence.
  B. Divide each net fluorescence by the average net fluorescence of Thyrotrol-norm. Then multiply by mean value for Thyrotrol-norm (from package insert) to get % T-3 Uptake. Euthyroid range: 35.0–45.0% T-3 Uptake $$\frac{\text{Net Fluorescence (Unknown)}}{\text{Net Fluorescence (Norm. Control)}} \times$$

% T − 3 uptake value for normal

C. % Binding of Antibody Column:

$$\frac{\text{Fluorescence Max. Binding}}{\text{Fluorescence Totals}} \times 100 = \% \text{ column binding}$$

Numerous modifications and variations of the present invention are possible in light of the above teachings, and, therfore, within the scope of the appended claims, the invention may be practiced otherwise than as particularly described.

What is claimed is:

1. A tracer for use in an assay comprising: a chromogen conjugated to a ligand through a spacer radical, said spacer radical for conjugating the chromogen to the ligand being derived from an amino acid and having the following structural formula:

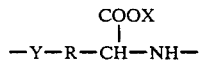

wherein X is selected from the group consisting of hydrogen, ammonium, amine salt and metal cations;

Y is selected from the group consisting of —NH— and

and R is selected from the group consisting of substituted and unsubstituted divalent hydrocarbon radicals having no more than 13 carbon atoms and wherein —R— and —CH— may be linked to form a carbocyclic radical.

2. The tracer of claim 1 wherein the chromogen is a fluorescein dye.

3. The tracer of claim 2 wherein R is an alkylene group having 4 carbon atoms and Y is —NH—.

4. The tracer of claim 3 wherein the ligand is triiodothyronine.

5. The tracer of claim 3 wherein the ligand is thyroxine.

6. The tracer of claim 3 wherein the ligand is digoxigenin.

7. The tracer of claim 1 wherein R is alkylene.

8. The tracer of claim 7 wherein the chromogen is a fluorescent dye.

9. The tracer of claim 8 wherein Y is —NH—.

10. The tracer of claim 9 wherein R is an alkylene group having from 2 to 6 carbon atoms.

11. The tracer of claim 10 wherein the fluorescent dye is a fluorescein dye.

12. The tracer of claim 1 wherein the tracer is N-α-(3-digoxigeninyl)-N-ε-[5(6)-carboxyfluoresceinoyl]-lysine.

13. The tracer of claim 1 wherein the tracer is carboxyfluorescein-lysylamide-3-ketodigoxigenin.

14. The tracer of claim 1 wherein the tracer is carboxyfluorescein-lysylamide-3,3′,5-triiodo-L-thyronine.

15. The tracer of claim 1 wherein the tracer is carboxyfluorescein-lysylamide-3,3′,5-triiodo-N-acetyl-L-thyronine.

16. The tracer of claim 1 wherein the tracer is N-α-(3-digoxigeminyl-N-ε-(dichlorotriazinylaminofluoresceinyl)-lysine.

17. The assay of claim 1 wherein during the assay the tracer is passed through a flow through chamber including a binder for the tracer.

18. The assay of claim 17 wherein the chromogen is a fluorescein dye.

19. The assay of claim 18 wherein R is an alkylene group having 4 carbon atoms and Y is —NH—.

20. The assay of claim 19 wherein the ligand is triiodothyronine and wherein the assay is a $T_3$ uptake assay for $T_3$ serum binding.

21. The assay of claim 19 wherein the ligand is thyroxine and wherein the analyte is thyroxine.

22. The assay of claim 19 wherein the ligand is digoxigenin and wherein the analyte is digoxin.

23. The assay of claim 17 wherein R is alkylene.

24. The assay of claim 23 wherein the chromogen is a fluorescent dye.

25. The assay of claim 24 wherein Y is —NH—.

26. The assay of claim 25 wherein R is an alkylene group having from 2 to 6 carbon atoms.

27. The assay of claim 26 wherein the fluorescent dye is a fluorescein dye.

28. The assay of claim 17 wherein the tracer is carboxyfluorescein-lysylamide-N-acetyl-L-thyroxine and wherein the analyte is thyroxine.

29. The assay of claim 17 wherein the tracer is N-60 -(3-digoxigeninyl)-N-ε-[5(6)-carboxylfluoresceinoyl]-lysine and wherein the analyte is digoxin.

30. The assay of claim 17 wherein the tracer is carboxyfluorescein-lysylamide-3,3′,5-triiodo-L-thyronine and wherein the assay is a $T_3$ uptake assay for $T_3$ serum binding proteins.

31. The assay of claim 17 wherein the tracer is carboxyfluorescein-lysylamide-3,3′,5-triiodo-N-acetyl-L-thyronine and wherein the assay is a $T_3$ uptake assay for $T_3$ serum binding proteins.

32. A process for determining an analyte, comprising: contacting analyte and tracer with a binder for at least the analyte, said tracer being comprised of a chromogen conjugated to a ligand through a spacer radical, said ligand being bound by one of the analyte and the binder, said spacer radical being derived from an amino acid and having the structural formula as defined in claim 1, said contacting binding a portion of the tracer; and determining at least one of bound and unbound tracer to determine analyte.

33. The process of claim 32 wherein the binder is a binder for both the analyte and tracer.

34. The process of claim 33 wherein bound and unbound tracer pass through a flow through chamber containing an adsorbent for the unbound tracer.

35. The process of claim 32 wherein the chromogen is a fluorescent dye.

36. The process of claim 35 wherein the analyte has a molecular weight of no greater than 2,000.

37. A reagent kit for use in an assay for an analyte, comprising:
a package, said package containing a binder for the analyte and a tracer for determining the analyte, said tracer being a tracer as defined in claim 1.

38. A regent kit for use in an essay for an analyte, comprising:
a package, said package containing a binder for the analyte and a tracer for determining the analyte, said tracer being a tracer as defined in claim 3.

39. A reagent kit for use in an assay for an analyte, comprising:
a package, said package containing a binder for the analyte and a tracer for determining the analyte, said tracer being a tracer as defined in claim 4.

40. A reagent kit for use in an assay for an analyte, comprising:
a package, said package containing a binder for the analyte and a tracer for determining the analyte, said tracer being a tracer as defined in claim 5.

41. A reagent kit for use in an assay for an analyte, comprising:
a package, said package containing a binder for the analyte and a tracer for determining the analyte, said tracer being a tracer as defined in claim 6.

42. A reagent kit for use in an assay for an analyte, comprising:
a package, said package containing a binder for the analyte and a tracer for determining the analyte, said tracer being a tracer as defined in claim 11.

* * * * *